(12) United States Patent
Chen et al.

(10) Patent No.: US 6,677,462 B2
(45) Date of Patent: Jan. 13, 2004

(54) ASYMMETRIC SYNTHESIS OF KAVALACTONES

(75) Inventors: Shoujun Chen, Billerica, MA (US); Lijun Sun, Harvard, MA (US); Joel McCleary, The Plains, VA (US)

(73) Assignee: Kava Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 09/923,462

(22) Filed: Aug. 6, 2001

(65) Prior Publication Data

US 2003/0060633 A1 Mar. 27, 2003

(51) Int. Cl.$^7$ .................. C07D 309/30; C07C 69/76; C07C 69/72; C07C 45/00; C07F 9/02
(52) U.S. Cl. .................. 549/292; 560/106; 560/178; 568/8; 568/17; 568/445
(58) Field of Search .................. 514/264, 262, 514/263, 460; 424/195.1; 560/178, 106; 568/8, 17, 445; 549/292

(56) References Cited

U.S. PATENT DOCUMENTS 5,977,120 A * 11/1999 Giles .................. 514/264

OTHER PUBLICATIONS

Spino, et al, Tetrahedron Letters, vol. 37, # 36, pp. 6503–6506 (1996).*

Evans et al, JACS, 110, pp. 3560–3578 (1988).*

* cited by examiner

Primary Examiner—Johann Richter
Assistant Examiner—Sikarl A. Witherspoon
(74) Attorney, Agent, or Firm—Fish & Richardson PC

(57) ABSTRACT

This invention relates to preparation of enantio-enriched compounds, and more particularly to enantio-enriched kavalactone compounds and derivatives thereof. The methods provide compounds that are useful as reagents, or building blocks, in the construction of other enantio-enriched compounds.

51 Claims, No Drawings

ASYMMETRIC SYNTHESIS OF KAVALACTONES

BACKGROUND

It is believed that the use of kava (Piper methysticum Forst.) predates written history. The origination of the plant is attributed to the New Guinea/Indonesia area and it is believed that Polynesian explorers were responsible for its spread from island to island. Oceania (i.e., the Pacific island communities of Micronesia, Melanesia and Polynesia) is an area where islanders have been known for centuries to consume a drink, also called kava and derived from the root of kava, in ceremonies and celebrations due to its reported calming effect and ability to promote sociability. The root and the drink were apparently first described in the Western world by Captain James Cook as a result of his exploration of the South Seas in 1768. Many myths and anecdotal stories surround the use of kava, and these vary from culture to culture.

In recent years, the Kava plant has been scientifically scrutinized, with certain of its active constituents being identified. The psychoactive ingredients of the Kava root have been identified as a class of structurally related chemical compounds known as kavalactones, including compounds such as compounds 1 and 2 (below). At least sixteen kavalactones have been identified to date, including kawain, dihydrokawain (a.k.a. marindinin), methysticin, dihydromethysticin, yangonin, and desmethoxyyangonin. These compounds are neutral, nitrogen-poor compounds that may be specifically referred to as substituted alpha.-pyrones. The lactone ring is substituted by a methoxy group in the C-4 position, and the compounds vary in their substitution by either a styryl residue (e.g., yangonin, desmethy-oxyyangonin, kawain, and methysticin) or by a phenylethyl residue (e.g., dihydrokawain and dihydromethysticin) at the C-6 position.

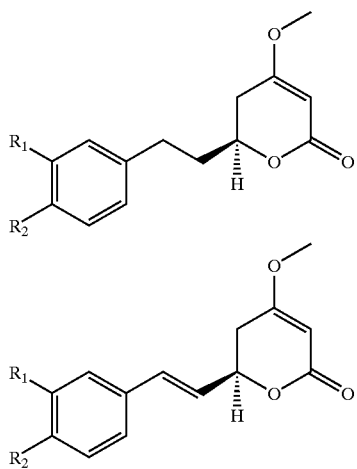

1: R1– R2 = H
2: R1, R2 = OCH2O

The absolute stereochemistry of the lactones was established by chemical degradation to (+)-malic acid. Judging from the positive cotton effect of the lactones in circular dichroism, the chiral center of C-6 of the lactones was assigned to be the R configuration.

Although the synthesis of racemic kawain or dihydrokawain was reported in the 1970's (See, T. Izawa and T. Mukaiyama, *Chemistry Letters* 1975, 161–164; Z. H. Israili and E. E. Smissman, *J. Org. Chem.*, 1976, 41(26), 4070–4073), the asymmetric synthesis of (S)-(+)-dihydrokawain was not realized until 1996 (See, C. Spino, N. Mayes and H. Desfosses, *Tetrahedron Letters*, 1996, 37(36), 6503–6506). A key intermediate for the asymmetric kavalactone synthesis is (S)-(+)-3-hydroxy-5-aryl-pentanoic acid methyl ester, Compound 3. In order to procure this intermediate in non-racemic form, an enantioselective method of some type (e.g., chiral separation, purification, derivatization, or asymmetric reduction) is necessary. In their synthesis, Spino et al. employed the reduction conditions of Noyori (see, R. Noyori, *Science* 1990, 248, 1194), however, very harsh conditions are required (e.g., 100° C., 10–100 atm) and it was reported that without the addition of HCl, no product was detected. In order to explore the potential medicinal application of the optically pure kavalactones and to conduct structure-activity relationship (SAR) studies of their analogs, a more practical and facile approach to the asymmetric synthesis of such chiral lactones is desirable.

SUMMARY

This invention relates to preparation of enantio-enriched compounds, and more particularly to enantio-enriched kavalactone compounds and derivatives thereof. The methods provide compounds that are useful as reagents, or building blocks, in the construct of other enantio-enriched compounds. The methods delineated herein demonstrate for the first time the application of chiral organoborane reducing agents to asymmetric reduction of β-keto ester compounds, which are important intermediates that can be further elaborated to kavalactones of increased optical purity.

In one embodiment, the invention relates to a method of making a compound comprising reacting a compound of formula (II),

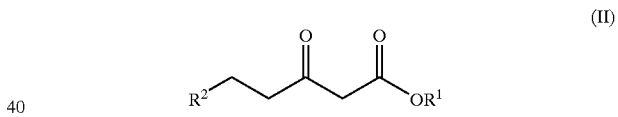

(II)

wherein
R$^1$ is independently alkyl, alkenyl, alkynyl, cycloalkyl, arylalkyl, or heteroarylalkyl;
R$^2$ is independently alkyl, aryl, arylalkyl, heteroaryl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)$_n$R$^6$, NO$_2$, CN, halo, NR$^6$C(O)R$^6$, or NR$^6$S(O)$_n$R$^6$;
Each R$^6$ is independently alkyl, alkenyl, alkynyl, cycloalkyl, aryl, heterocyclyl, arylalkyl, or heteroarylalkyl, each optionally substituted with 1–4 independent substituents selected from the group hydroxy, mercapto, amino, alkoxy, carboxylic acid, ester, amido, N-alkyl-substitited amido, halo, nitro, and nitrile; and
n is 1 or 2;
with a chiral borane reducing agent to give a compound of formula (I):

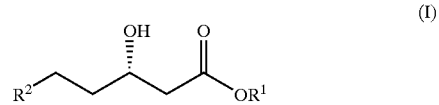

(I)

wherein R$^1$ and R$^2$ are as defined above. The reaction can be performed at room temperature.

In another embodiment, the method is any method delineated herein further comprising converting a compound of formula (I) to a compound of formula (III):

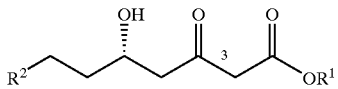
(III)

wherein
R$^1$ is independently alkyl, arylalkyl, or heteroarylalkyl;
R$^2$ is independently alkyl, aryl, arylalkyl, heteroaryl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)$_n$R$^6$, NO$_2$, CN, halo, NR$^6$C(O)R$^6$, or NR$^6$S(O)$_n$R$^6$;
Each R$^6$ is independently alkyl, alkenyl, alkynyl, cycloalkyl, aryl, heterocyclyl, arylalkyl, or heteroarylalkyl, each optionally substituted with 1–4 independent substituents selected from the group hydroxy, mercapto, amino, alkoxy, carboxylic acid, ester, amido, N-alkyl-substitited amido, halo, nitro, and nitrile; and
n is 1 or 2.

In another embodiment, the method is any method delineated herein wherein the compound of formula (I) is reacted with a nucleophile, or salt thereof, of formula (IV):

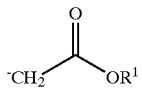
(IV)

wherein
R$^1$ is independently alkyl, arylalkyl, or heteroarylalkyl; to give the compound of formula (III). In one aspect the nucleophile of formula (IV) is the lithium salt of the t-butylacetate anion.

In another embodiment, the method is any method delineated herein further comprising converting a compound of formula (I) to a compound of formula (V):

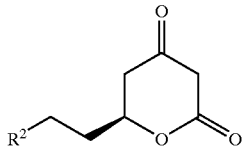
(V)

wherein
R$^2$ is independently alkyl, aryl, arylalkyl, heteroaryl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)$_n$R$^6$, NO$_2$, CN, halo, NR$^6$C(O)R$^6$, or NR$^6$S(O)$_n$R$^6$;
Each R$^6$ is independently alkyl, alkenyl, alkynyl, cycloalkyl, aryl, heterocyclyl, arylalkyl, or heteroarylalkyl, each optionally substituted with 1–4 independent substituents selected from the group hydroxy, mercapto, amino, alkoxy, carboxylic acid, ester, amido, N-alkyl-substitited amido, halo, nitro, and nitrile; and
n is 1 or 2.
The method of converting includes reacting with an acid catalyst, such as an inorganic acid (e.g., HCl, H$_2$SO$_4$) or an organic acid (e.g., an acetic acid or a sulfonic acid (e.g., trifluoroacetic acid, p-toluenesulfonic acid, or camphorsulfonic acid)).

In another embodiment, the method is any method delineated herein further comprising converting a compound of formula (I) to a compound of formula (VI) (alternatively, including via a compound of formula (V)):

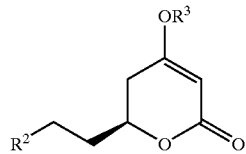
(VI)

wherein
R$^2$ is independently alkyl, aryl, arylalkyl, heteroaryl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)nR$^6$, NO$_2$, CN, halo, NR$^6$C(O)R$^6$, or NR$^6$S(O)$_n$R$^6$;
n is 1 or 2;
R$^3$ is independently H, alkyl, arylalkyl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)$_n$R$^6$, NO$_2$, CN, halo, NR$^6$C(O)R$^6$, or NR$^6$S(O)$_n$R$^6$; and
Each R$^6$ is independently alkyl, alkenyl, alkynyl, cycloalkyl, aryl, heterocyclyl, arylalkyl, or heteroarylalkyl, each optionally substituted with 1–4 independent substituents selected from the group hydroxy, mercapto, amino, alkoxy, carboxylic acid, ester, amido, N-alkyl-substitited amido, halo, nitro, and nitrile. In other embodiments, the method is any method delineated herein wherein the converting includes reacting with an alkylating agent in the presence of a base, wherein the alkylating agent is an alkyl halide, and wherein the alkylating agent is an alkyl sulfate.

In other embodiments, the method is any method delineated herein wherein the chiral borane reducing agent is a borane-dimethylsulfide complex; wherein the chiral borane reducing agent is a borane-dimethylsulfide complex derived from a chiral 2-pyrrolidinemethanol derivative; wherein the chiral borane reducing agent is an oxazapyrrolidinyl borane; wherein the chiral borane reducing agent is a borane-dimethylsulfide complex derived from (S)-(−)-α,α,-diphenyl-2-pyrrolidinemethanol; wherein the chiral borane is derived from (S)-(−)-α,α,-diaryl-2-pyrrolidinemethanol; or wherein the chiral borane is derived from (S)-(−)-α,α,-dialkyl-2-pyrrolidinemethanol.

In other embodiments, the method is any method delineated herein wherein the compound is a kavalactone (e.g., dihydrokawain, (S)-(+)-dihydrokawain, or dihydrokawain or dihydromethysticin); wherein the compound is a compound present in the extract of kava kava; wherein the compound is a kavalactone derivative compound; wherein the compound is an active kavalactone derivative compound; wherein the compound is an intermediate for production of a kavalactone; or wherein the compound is an intermediate for production of a compound present in the extract of kava kava. The invention also relates to methods of making a kavalactone (e.g., dihydrokawain, (S)-(+)-dihydrokawain, or dihydrokawain or dihydromethysticin), or making an enantio-enriched kavalactone including any of the methods delineated herein.

In other embodiments, the method is any method delineated herein comprising reacting a compound of formula (VIII):

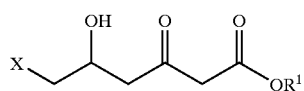
(VIII)

wherein

R¹ is independently alkyl, arylalkyl, or heteroarylalkyl;

X is a leaving group;

with a chiral borane reducing agent to give a compound of formula (VII)

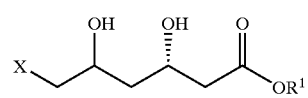
(VII)

wherein R¹ and X are as defined above. The reaction can be performed at room temperature.

In other embodiments, the method is any method delineated herein further comprising converting a compound of formula (VII) to a compound of formula (IX):

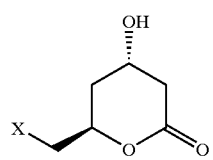
(IX)

wherein X is a leaving group.

In other embodiments, the method is any method delineated herein further comprising converting a compound of formula (VII) to a compound of formula (X) (alternatively, including via a compound of formula (IX)):

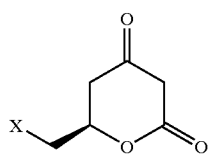
(X)

wherein

X is a leaving group.

The method includes those delineated herein wherein the converting includes reacting with an oxidizing agent.

In other embodiments, the method is any method delineated herein further comprising converting the compound of formula (VII) to a compound of formula (XI) (alternatively, including via a compound of any of formulae (IX), (X), or combination thereof):

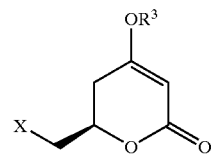
(XI)

wherein

R³ is independently H, alkyl, arylalkyl, heteroarylalkyl; and

X is a leaving group.

The method includes those delineated herein wherein the converting includes reacting with an alkylating agent in the presence of a base.

In other embodiments, the method is any method delineated herein further comprising converting the compound of formula (VII) to a compound of formula (XII) (alternatively, including via a compound of any of formulae (IX–XI), or combination thereof):

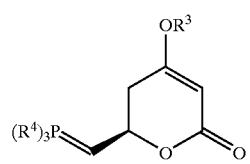
(XII)

wherein

R³ is independently H, alkyl, arylalkyl, heteroarylalkyl; and each R⁴ is independently alkyl or aryl.

The method includes those delineated herein wherein the converting includes reacting with a triaryl-substituted phosphine.

In other embodiments, the method is any method delineated herein further comprising reacting a compound of formula (XIV):

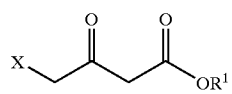
(XIV)

wherein

R¹ is independently alkyl, arylalkyl, or heteroarylalkyl; and

X is a leaving group (or alternatively, OR⁶, as defined below for formula (XVI));

with a chiral borane reducing agent to give a compound of formula (XIII).

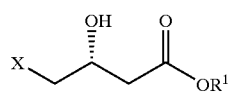
(XIII)

wherein R¹ and X are as defined above.

In other embodiments, the method is any method delineated herein further comprising converting a compound of formula (XIII) to a compound of formula (XV):

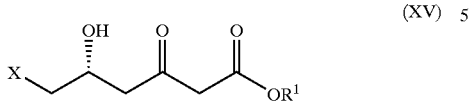

(XV)

wherein
$R^1$ is independently alkyl, arylalkyl, or heteroarylalkyl; and
X is a leaving group (or alternatively, $OR^6$, as defined for formula (XVI)).

In other embodiments, the method is any method delineated herein wherein the compound of formula (XIII) is reacted with a nucleophile, or salt thereof, of formula (IV):

(IV)

wherein
$R^1$ is independently alkyl, arylalkyl, or heteroarylalkyl; to give the compound of formula (XV).

In other embodiments, the method is any method delineated herein further comprising converting a compound of formula (XIII) to a compound of formula (XVI) (alternatively including via a compound of formula (XV)):

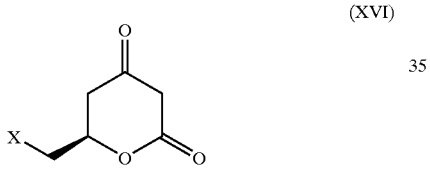

(XVI)

wherein
X is $OR^6$; and
Each $R^6$ is independently alkyl, alkenyl, aryl, arylalkyl, or heteroarylalkyl, each optionally substituted with 1–4 independent substituents selected from the group hydroxy, mercapto, amino, alkoxy, carboxylic acid, ester, amido, N-alkyl-substitited amido, halo, nitro, and nitrile.

In other embodiments, the method is any method delineated herein further comprising converting a compound of formula (XIII) to a compound of formula (XVII) (alternatively, including via a compound of any of formulae (XV), (XVI), or combination thereof):

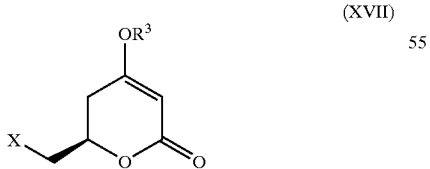

(XVII)

wherein
X is $OR^6$;
$R^3$ is independently H, alkyl, arylalkyl, heteroarylalkyl, each optionally substituted with 1 to 4 independent $NR^6R^6$, $C(O)NR^6R^6$, $OR^6$, $SR^6$, $C(O)OR^6$, $C(O)R^6$, $SO_nR^6$, $NO_2$, CN, halo, $NR^6C(O)R^6$, or $NR^6S(O)_nR^6$;

n is 1 or 2; and
Each $R^6$ is independently alkyl, alkenyl, aryl, arylalkyl, or heteroarylalkyl, each optionally substituted with 1–4 independent substituents selected from the group hydroxy, mercapto, amino, alkoxy, carboxylic acid, ester, amido, N-alkyl-substitited amido, halo, nitro, and nitrile.

The method includes those delineated herein wherein the converting includes reacting with an alkylating agent in the presence of a base.

In other embodiments, the method is any method delineated herein further comprising converting a compound of formula (XIII) to a compound of formula (XVIII) (alternatively including via a compound of any of formulae (XV–XVII), or combination thereof):

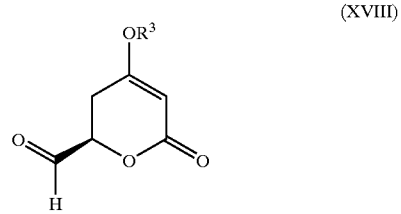

(XVIII)

wherein
$R^3$ is independently H, alkyl, arylalkyl, heteroarylalkyl, each optionally substituted with 1 to 4 independent $NR^6R^6$, $C(O)NR^6R^6$, $OR^6$, $SR^6$, $C(O)OR^6$, $C(O)R^6$, $S(O)_nR^6$, $NO_2$, CN, halo, $NR^6C(O)R^6$, or $NR^6S(O)_nR^6$;

n is 1 or 2; and
Each $R^6$ is independently alkyl, alkenyl, aryl, arylalkyl, or heteroarylalkyl, each optionally substituted with 1–4 independent substituents selected from the group hydroxy, mercapto, amino, alkoxy, carboxylic acid, ester, amido, N-alkyl-substitited amido, halo, nitro, and nitrile.

The method includes those delineated herein wherein the converting includes reacting with an oxidizing agent.

In other embodiments, the invention relates to a composition comprising a compound produced according to any of the methods delineated herein; a composition comprising a compound produced according to any of the methods delineated herein, wherein the composition is a nutraceutical food product; and a composition comprising a compound produced according to any of the methods delineated herein wherein the composition is a topical ointment.

The details of one or more embodiments of the invention are set forth in the accompanying drawings and the description below. Other features, objects, and advantages of the invention will be apparent from the description and drawings, and from the claims.

DETAILED DESCRIPTION

A chiral borane reducing agent is any organoborane reagent that provides a reduced product that is essentially of a single enantiomeric form, or is provides a mixture of reduction products that are predominately one enantiomeric form relative to the other. The organoborane can be as a borane -dimethyl sulfide complex. The borane can be a complex that is either formed in situ immediately prior to use, or can be a complex that is formed, and stored (either neat, or as a solution in a suitable solvent) for use at a later time. The chiral borane reducing agent can be derived from 2-pyrrolidinemethanol, or derivatives thereof. Such agents can also be referred to as oxazapyrrolidinyl boranes. Chiral organoboranes are known in the art, for example, substituted 2-pyrrolidinemethanol derivatives such as (S)-(−)-α,α,-diphenyl-2-pyrrolidinemethanol are suitable for use in the methods delineated herein (see, E. J. Corey, R. K. Bakshi and S. Shibata, *J. Am. Chem. Soc.,* 1987, 109, 5551–5553).

Acids and bases useful in the methods herein are known in the art. Acid catalysts are any acidic chemical, which can be inorganic (e.g., hydrochloric, sulfuric, nitric acids) or organic (e.g., camphorsulfonic acid, p-toluenesulfonic acid, acetic acid) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., Cl—, Br—, F—), hydroxy, alkoxy (e.g., -OMe, —O-t-Bu), acyloxy anions (e.g., —OAc, —OC(O)CF$_3$), sulfonates (e.g., mesyl, tosyl), acetamides (e.g., -NHC(O)Me), carbamates (e.g., N(Me)C(O)Ot-Bu), phosphonates (e.g., -OP(O)(OEt)$_2$), water or alcohols (protic conditions), and the like.

A kavalactone is any lactone-containing chemical compound derived from kava kava root. A kavalactone derivative compound is a compound having a kavalactone core chemical structure (e.g., a compound of formula VI herein, a substituted alpha.-pyrone) which is not a kavalactone found in the extract of the kava kava root. A dihydrokawain derivative compound is a compound having a dihydrokawain core chemical structure (e.g., a compound of any of formula VI herein), which is not dihydrokawain.

Using the methods herein, compounds can be produced in enantio-enriched form, that is one enantiomer is preferentially produced relative to the respective other enantiomer. In certain instances, one enantiomer is produced essentially exclusively relative to the other. Methods for determining the optical purity of a reaction product mixture are known in the art and include spectroscopic analytical techniques as well as chemical derivatization techniques. The relative abundance of each enantiomer can be reported in terms of the enantiomeric excess ("e.e.") of one enantiomer.

Oxidizing agents are any reagent that is capable of effecting the oxidation of the functional group at issue to a functional group of a higher oxidation state, for example, converting an alcohol group to an aldehyde or carboxylic acid. Oxidation agents are known in the art, including in the references cited herein. The oxidizing agents may be prepared in situ immediately prior to use (e.g., Swern reagent) or may be prepared and stored (e.g., Dess-Martin reagent).

The term "halo" refers to any radical of fluorine, chlorine, bromine or iodine. The term "alkyl" refers to a hydrocarbon chain that may be a straight chain or branched chain, containing the indicated number of carbon atoms. For example, C1–C10 indicates that the group may have from 1 to 10 (inclusive) carbon atoms in it. The term "lower alkyl" refers to a C1–C6 alkyl chain. The term "alkenyl" refers to an unsaturated hydrocarbon chain that may be a straight chain or branched chain, containing the indicated number of carbon atoms. The term "alkynyl" refers to an unsaturated hydrocarbon chain that may be a straight chain or branched chain, containing the indicated number of carbon atoms and at least one carbon-carbon triple bond. The term "alkoxy" refers to an —O-alkyl radical. The term "ester" refers to a C(O)O-alkyl or C(O)O-aryl group. An "amido" is an C(O) NH$_2$, an "N-alkyl-substitited amido" is of the formula C(O) N(H)(alkyl).

The term "cycloalkyl" refers to a 6-carbon monocyclic or 10-carbon bicyclic nonaromatic ring system wherein 0, 1, 2, 3, or 4 atoms of each ring may be substituted by a substituent. Examples of cycloalkyl groups include cyclopentyl, cyclohexyl, cyclohexenyl, bicyclo[2.2.1]hept-2-enyl, dihydronaphthalenyl, benzocyclopentyl, and the like.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "heteroaryl" refers to an aromatic 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, wherein 0, 1, 2, 3, or 4 atoms of each ring may be substituted by a substituent. Examples of heteroaryl groups include pyridyl, furyl or furanyl, imidazolyl, benzimidazolyl, thienyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5–8 membered monocyclic, 8–12 membered bicyclic, or 11–14 membered tricyclic ring system comprising 1–3 heteroatoms if monocyclic, 1–6 heteroatoms if bicyclic, or 1–9 heteroatoms if tricyclic, said heteroatoms selected from O, N, or S, wherein 0, 1, 2, 3, or 4 atoms of each ring may be substituted by a substituent. Examples of heterocyclyl groups include tetrahydrofuryl, piperidinyl, pyrrolidinyl, morpholinyl, dihydrothiophenyl, and the like.

Aryl, heteroaryl, cycloalkyl, and heterocyclyl groups can be substituted by substituent groups, including for example, 1–4 independent substituents selected from the group hydroxy, mercapto, amino, alkoxy, carboxylic acid, ester, amido, N-alkyl-substitited amido, halo, nitro, and nitrile; or 1 to 4 independent NR$^6$R$^6$, C(O)NR$^6$R$^6$, OR$^6$, SR$^6$, C(O) OR$^6$, C(O)R$^6$, S(O)$_n$R$^6$, NO$_2$, CN, halo, NR$^6$C(O)R$^6$, or NR$^6$S(O)$_n$R$^6$; wherein n is 1 or 2; and each R$^6$ is independently alkyl, alkenyl, aryl, arylalkyl, or heteroarylalkyl, each optionally substituted with 1–4 independent substituents selected from the group hydroxy, mercapto, amino, alkoxy, carboxylic acid, ester, amido, N-alkyl-substitited amido, halo, nitro, and nitrile.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into food or beverage products, storable intermediates for use in production of derivative compounds). The compounds produced by the methods herein can be incorporated into compositions, including beverages, tablets, crèmes, or ointments for administration to a subject (e.g., human, animal). Such compositions (e.g., nutraceuticals) are useful for providing to the subject desirable health or other physiological benefits that are associated with kavalactones.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally comprise steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography).

As can be appreciated by the skilled artisan, the synthetic schemes herein are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

Embodiments are further described in the following representative examples, which do not limit the scope of the invention described in the claims.

EXAMPLES

Example 1

Synthesis of S-(+)-4-Methoxy-6-phenethyl-5,6-dihydro-pyran-2-one. (S-+-Dihydrokawain)

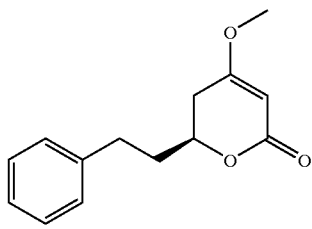

To a stirred solution of (S)-(−)-α,α-diphenyl-2-pyrrolidinemethanol (770 mg, 3 mmol) in dry THF (100 mL) was added 2 M THF solution of borane-dimethylsulfide complex (11 mL, 22 mmol) at rt under $N_2$. After being stirred at rt for 16 h, a solution of 3-Oxo-5-phenyl-pentanoic acid methyl ester (JACS, 1974, 1082–1087) (6.5 g, 31.5 mmol) in dry THF (20 mL) was added dropwise at rt over a period of 1 h. The resultant clear solution was stirred at rt for another 30 min and was then cooled to 0° C. in an ice bath. The reaction was quenched by the addition of MeOH (90 mL) and the reaction pot was concentrated under reduced pressure. The residue was taken up with EtOAc (200 mL) and washed successively with $H_2O$ (100 mL), citric acid (100 mL), 5% $NaHCO_3$ (100 mL) and brine (100 mL). After being dried over $Na_2SO_4$, the solvent was removed to afford an oil. Flush column chromatography purification on silica gel gave 3-Hydroxy-5-phenyl-pentanoic acid methyl ester as an oil (3.3 g, 51%) with 92% e.e. (judged from the corresponding Mosher's ester). $^1$H NMR (300 MHz, $CDCl_3$) δ1.6–1.9 (m, 2H), 2.4–2.6 (m, 2H), 2.65–2.9 (m, 2H), 3.05 (d, 1H, J=6), 3.7 (s, 3H), 3.95–4.10 (m, 1H), 7.10–7.35 (m, 5H). ESMS calcd ($C_{12}H_{16}O_3$): 208.1; found: 209.1 (M+H)$^+$.

A solution of 2.0 M LDA in heptane/THF/ethylbezene (9.4 mL, 18.8 mmol) was added slowly to a stirred solution of tert-butylacetate (2.18 g, 18.8 mmol) in dry THF (20 mL) under $N_2$ at −78° C. After being stirred at −78° C. for 25 min., a solution of the above made 3-hydroxy-5-phenyl-pentanoic acid methyl ester (1.3 g, 6.25 mmol) in dry THF (10 mL) was then added through a cannula. The resultant clear solution was stirred at −78° C. for 1 h and then at −55° C. for another 1 h. The reaction was quenched by the addition of 20% aqueous acetic acid (20 mL). Two layers were separated and the aqueous layer was extracted with EtOAc (3×30 mL). Combined organic layer was washed with $H_2O$ (50 mL, brine (50 mL, dried with sodium sulfate, and then concentrated to leave an oil. Flush column chromatography purification on silica gel (4:1 Hexane/EtOAc to 2:1 Hexane/EtOAc) afforded the intermediate 5-Hydroxy-3-oxo-7-phenyl-heptanoic acid tert-butyl ester as a colorless oil (1.74 g, 95%). $^1$H NMR (300 MHz, $CDCl_3$) δ1.45 (s, 9H), 1.6–1.9 (m, 2H), 2.50–2.85 (m, 4H), 3.35 (s, 3 H), 3.95–4.10 (m, 1H), 7.10–7.30 (m, 5H). ESMS calcd ($C_{17}H_{24}O_4$): 292.2; found: 291.2 (M−H)$^+$.

A solution of 5-hydroxy-3-oxo-7-phenyl-heptanoic acid tert-butyl ester (0.96 g, 3.3 mmol) and TFA (0.38 g, 3.3 mmol) in DCM (60 mL) was stirred at rt for 18 h. Removal of the volatile components under reduced pressure afforded the product 6-Phenethyl-dihydro-pyran-2,4-dione as an off white solid (0.56 g, 78%). $^1$H NMR (300 MHz, $CDCl_3$) δ1.9–2.2 (m, 2H), 2.4–2.7 (m, 2H), 2.75–2.95 (m, 2 H), 3.5 (q, 2H), 4.55–4.65(m, 1H), 7.10–7.35 (m, 5H). ESMS calcd ($C_{13}H_{14}O_3$): 218.1; found: 219.1 (M+H)$^+$.

A suspension of $K_2CO_3$(0.33 g, 2.4 mmol), dimethyl sulfate (0.22 g, 1.76 mmol) and 6-Phenethyl-dihydro-pyran-2,4-dione (0.35 g, 1.6 mmol) in dry acetone was stirred at rt for 18 h. Reaction mixture was filtered and washed with acetone. Filtrate and washings were combined and then concentrated to give an oil. Flush column chromatography purification on silica gel (4:1 Hexane/EtOAc to 1:1 Hexane/EtOAc) furnished the product S-(+)-4-Methoxy-6-phenethyl-5,6-dihydro-pyran-2-one as a white solid (0.36 g, 97%). $[\alpha]^{25}$=+29.01 (0.2433, CHCl$_3$); lit. +31. $^1$H NMR (300 MHz, CDCl$_3$) δ1.85–2.2 (m, 2 H), 2.25–2.55 (m, 2H), 2.70–2.95 (m, 2H), 3.7 (s, 3 H), 4.3–4.4 (m, 1H), 5.15 (s, 1H), 7.15–7.35 (m, 5H). ESMS calcd (C$_{14}$H$_{16}$O$_3$): 232.1; found: 233.1 (M+H)$^+$.

Example 2

Synthesis of S-(+)-4-isopropoxy-6-phenethyl-5,6-dihydro-pyran-2-one

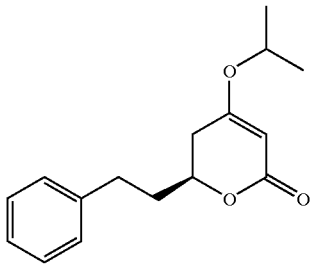

To a stirred solution of 6-Phenethyl-dihydro-pyran-2,4-dione (0.22 g, 1.0 mmol) in dry DMF (5 mL) and THF (2 mL) was added NaH (60% in mineral oil, 61 mg, 1.5 mmol). The suspension was stirred at rt for 20 min. 2-Iodopropane (0.26 g, 1.5 mmol) was then added and the mixture was stirred at 45° C. for 18 h. The reaction mixture was diluted with EtOAc (80 mL) and washed with H$_2$O (2×50 mL), brine (50 mL), dried with Na$_2$SO$_4$ and concentrated to give an oil. Flush column chromatography purification on silica gel (4:1 Hexane/EtOAc to 2:1 Hexane/EtOAc) furnished the product S-(+)-4-isopropoxy-6-phenethyl-5,6-dihydro-pyran-2-one as a colorless syrup (0.12 g, 53%). $^1$H NMR (300 MHz, CDCl$_3$) δ1.3 (m, 6 H), 1.85–2.20 (m, 2H), 2.20–2.55 (m, 2H), 2.70–2.95 (m, 2 H), 4.3–4.5 (m, 2H), 5.10 (s, 1H), 7.15–7.35 (m, 5H). ESMS calcd (C$_{16}$H$_{20}$O$_3$): 260.1; found: 261.1 (M+H)$^+$.

Example 3

Synthesis of (S)-6-[2-(4-Fluoro-phenyl)-ethyl]-4-methoxy-5,6-dihydro-pyran-2-one

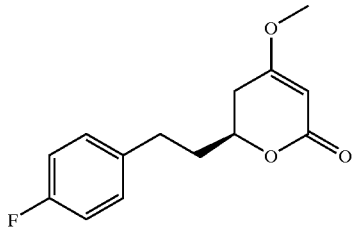

To a stirred suspension of NaH (60% suspension in mineral oil, 1.42 g, 36 mmol) in dry THF (50 mL) was added ethyl acetoacetate (4.3 g, 33 mmol) dropwise at 0° C. After 10 min stirring at this temperature, a 2.0 M solution of n-BuLi in cyclohexane (17.7 mL, 35 mmol) was added dropwise under N$_2$. The stirring was continued at 0° C. for 10 min., 4-fluorobenzyl bromide (9.45 g, 50 mmol) was then added dropwise at 0° C. The resultant solution was allowed to warm to rt. After 20 min, the reaction as quenched with 2 N HCl/Et$_2$O (20 mL/40 mL). Layers were separated, the aqueous layer was extracted with ether (3×50 mL). Combined ether solution was washed with H$_2$O (50 mL), brine (50 mL), and dried with Na$_2$SO$_4$. After removal of the solvent under reduced pressure, the resultant oily material was purified by flush column chromatography on silica gel (hexane to 4:1 hexane/EtOAc). The corresponding intermediate 5-(4-Fluoro-phenyl)-3-oxo-pentanoic acid ethyl ester was obtained as a colorless liquid (7.16 g, 92%). $^1$H NMR (300 MHz, CDCl$_3$) δ1.25 (t, 3H, J=7), 2.80–2.95 (m, 4H), 3.40 (s, 2H), 4.10–4.25 (m, 2H), 6.9–7.0 (m, 2H), 7.1–7.2 (m, 2H). ESMS calcd (C$_{13}$H$_{15}$FO$_3$): 238.1; found: 239.1 (M+H)$^+$.

A solution of (S)-(−)-α,α-diphenyl-2-pyrrolidinemethanol (240 mg, 0.97 mmol) and 2 M Borane-Dimethylsulfide complex (in THF, 3.4 mL, 6.8 mmol) in dry THF (50 mL) was stirred at rt under N$_2$ for 16 h. A solution of 5-(4-Fluoro-phenyl)-3-oxo-pentanoic acid ethyl ester (2.03 g, 8.57 mmol) in dry THF (20 mL) was then added dropwise at rt over a period of 1 h. The resultant clear solution was stirred at rt for another 35 min and was then cooled to 0° C. in an ice bath. The reaction was quenched by the addition of EtOH (40 mL) and was concentrated under reduced pressure. The residue was taken up with EtOAc (100 mL) and washed successively with H$_2$O (50 mL), 5% NaHCO$_3$ (50 mL), brine (50 mL), and then dried over Na$_2$SO$_4$. Removal of the solvent afforded an oil, which was purified by flush column chromatography on silica gel. The intermediate S-5-(4-Fluoro-phenyl)-3-hydroxy-pentanoic acid ethyl ester was obtained as a colorless oil (1.33 g, 65%). 1H NMR (300 MHz, CDCl$_3$) δ1.25 (t, 3H, J=7), 1.6–1.9 (m, 2H), 2.35–2.50 (m, 2H), 2.60–2.85 (m, 2H), 3.1 (d, 1H, J=5), 3.95–4.05 (m, 1H), 4.1–4.25 (m, 2H), 6.9–7.0 (m, 2H), 7.05–7.2 (m, 2H). ESMS calcd (C$_{13}$H$_{17}$FO$_3$): 240.1; found: 241.1 (M+H)$^+$.

To a stirred solution of tert-butylacetate (1.39 g, 12 mmol) in dry THF (20 mL) was added a solution of 2.0M LDA in heptane/THF/ethylbezene (6 mL, 12 mmol) under N$_2$ at −75° C. Stirring was continued at −75° C. for 25 min., a solution of S-5-(4-Fluoro-phenyl)-3-hydroxy-pentanoic acid ethyl ester (0.96 g, 4 mmol) in dry THF (10 mL) was then added through a cannula. The resultant clear solution was stirred at −50° C. for 2 h, quenched by the addition of 20% aqueous acetic acid (20 mL) at 0° C., extracted with EtOAc (3×30 mL). Combined extracts was washed with H$_2$O (50 mL), brine (50 mL, dried with sodium sulfate, and then concentrated to leave an oil. Flush column chromatography purification on silica gel (Hexane to 2:1 Hexane/EtOAc) afforded the intermediate 7-(4-Fluoro-phenyl)-5-hydroxy-3-oxo-heptanoic acid tert-butyl ester as a colorless oil (0.79 g, 61%). $^1$H NMR (300 MHz, CDCl$_3$) δ1.45 (s, 9H), 1.6–1.9 (m, 2H), 2.60–2.85 (m, 4H), 3.39 (s, 3 H), 3.95–4.15 (m, 1H), 6.95–7.10 (m, 2H), 7.1–7.2 (m, 2H). ESMS calcd (C$_{17}$H$_{23}$FO$_4$): 310.2; found: 309.2 (M−H)$^+$.

To a stirred solution of 7-(4-Fluoro-phenyl)-5-hydroxy-3-oxo-heptanoic acid tert-butyl ester (0.64 g, 2.06 mmol) in dry DCM was added TFA (0.24 g, 2.1 mmol) at 0° C. The resultant clear solution was stirred at rt for 16h. Removal of the volatile components under reduced pressure afforded the product 6-[2-(4-Fluoro-phenyl)-ethyl]-dihydro-pyran-2,4-dione as a white solid (0.32g, 66%). $^1$H NMR (300 MHz, CDCl$_3$) δ1.8–2.2 (m, 2H), 2.25–2.55 (m, 2H), 2.65–2.95 (m, 2H), 3.55 (dd, ~1H, J=10), 4.25–4.40(m, ~0.5H), 4.6–4.7 (m, ~0.5 H), 5.2 (s, ~0.5 H), 6.90–7.05 (m, 2H), 7.1–7.2 (m, 2H), 10.8 (br, ~0.5H). ESMS calcd (C$_{13}$H$_{13}$FO$_3$): 236.1; found: 237.1 (M+H)$^+$.

A suspension of K₂CO₃ (0.2 g, 1.5 mmol), dimethyl sulfate (0.14 g, 1.1 mmol) and 6-[2-(4-Fluoro-phenyl)-ethyl]-dihydro-pyran-2,4-dione (0.23 g, 0.97 mmol) in dry acetone was stirred at rt for 24 h. Non-dissoluble material was filtered and washed with acetone. Filtrate and washings were combined and concentrated to give an oil. Flush column chromatography purification on silica gel (4:1 Hexane/EtOAc to 1:1 Hexane/EtOAc) furnished the product S-6-[2-(4-Fluoro-phenyl)-ethyl]-4-methoxy-5,6-dihydro-pyran-2-one as a white solid (0.15 g, 62%). ¹H NMR (300 MHz, CDCl₃) δ1.82–2.15 (m, 2 H), 2.25–2.60 (m, 2H), 2.70–2.95 (m, 2H), 3.72 (s, 3 H), 4.3–4.4 (m, 1H), 5.15 (s, 1H), 6.95–7.05 (m, 2H), 7.12–7.21 (m, 2H). ESMS calcd (C₁₄H₁₅FO₃): 250.1; found: 251.1 (M+H)⁺.

Examples 4–9 below were synthesized following procedures analogous to the examples described above.

Example 4

Synthesis of (S)-4-Ethoxy-6-phenethyl-5,6-dihydro-pyran-2-one.

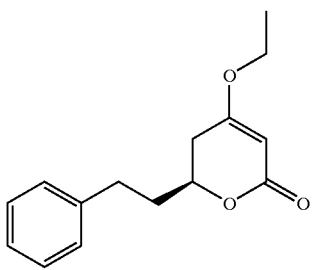

¹H NMR (300 MHz, CDCl₃) δ1.20 (t, 3H, J=7), 1.85–2.20 (m, 2 H), 2.25–2.60 (m, 2H), 2.70–2.95 (m, 2H), 3.84–4.00 (m, 2 H), 4.30–4.40 (m, 1H), 5.15 (s, 1H), 7.10–7.35 (m, 5H). ESMS calcd (C₁₄H₁₆O₃): 246.1; found: 247.1 (M+H)⁺.

Example 5

Synthesis of (S)-6-Phenethyl-4-trityloxy-5,6-dihydro-pyran-2-one

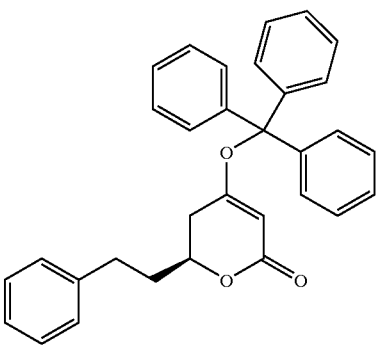

¹H NMR (300 MHz, CDCl₃) δ1.90–2.20 (m, 2 H), 2.35–2.60 (m, 2H), 2.70–2.95 (m, 2H), 3.84–4.00 (m, 2 H), 4.55–4.62 (m, 1H), 6.03 (s, 1H), 7.10–7.41 (m, 20 H). ESMS calcd (C₃₂H₂₂O₃): 460.2; found: 261.2 (M+H)⁺.

Example 6

Synthesis of (S)-6-[2-(2-Fluoro-phenyl)-ethyl]-dihydro-pyran-2,4-dione.

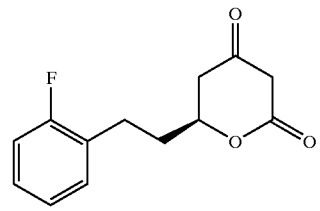

¹H NMR (300 MHz, CDCl₃) δ1.85–2.2 (m, 2H), 2.4–3.0 (m, 4H), 3.5 (q, 2H), 4.55–4.65(m, 1H), 6.95–7.30 (m, 4H). ESMS calcd (C₁₃H₁₃FO₃): 236.1; found: 237.1 (M+H)⁺.

Example 7

(S)-6-[2-(2-Fluoro-phenyl)-ethyl]-4-methoxy-5,6-dihydro-pyran-2-one

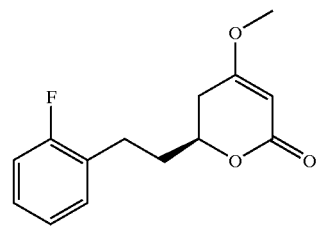

¹H NMR (300 MHz, CDCl₃) δ1.90–2.18 (m, 2 H), 2.25–2.60 (m, 2H), 2.75–3.00 (m, 2H), 3.75 (s, 3 H), 4.3–4.4 (m, 1H), 5.15 (s, 1H), 6.95–7.10 (m, 2H), 7.15–7.25 (m, 2H). ESMS calcd (C₁₄H₁₅FO₃): 250.1; found: 251.1 (M+H)⁺.

Example 8

Synthesis of (S)-6-[2-(3-Fluoro-phenyl)-ethyl]-dihydro-pyran-2,4-dione.

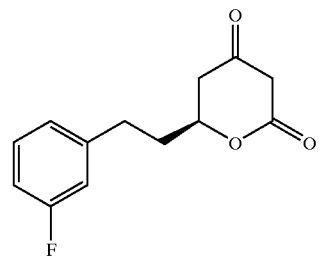

¹H NMR (300 MHz, CDCl₃) δ1.95–2.2 (m, 2H), 2.45–3.01 (m, 4H), 3.5 (q, 2H), 4.53–4.65(m, 1H), 6.90–7.05 (m, 3H), 7.21–7.35 (m, 1H). ESMS calcd (C₁₃H₁₃FO₃): 236.1; found: 237.1 (M+H)⁺.

Example 9

(S)-6-[2-(3-Fluoro-phenyl)-ethyl]-4-methoxy-5,6-dihydro-pyran-2-one

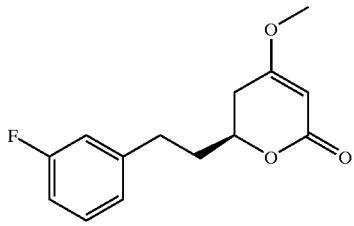

$^1$H NMR (300 MHz, CDCl$_3$) δ1.85–2.18 (m, 2 H), 2.25–2.58 (m, 2H), 2.70–2.95 (m, 2H), 3.72 (s, 3 H), 4.32–4.41 (m, 1H), 5.18 (s, 1H), 6.85–7.00 (m, 3H), 7.20–7.30 (m, 1H). ESMS calcd (C$_{14}$H$_{15}$FO$_3$): 250.1; found: 251.1 (M+H)$^+$.

A number of embodiments of the invention have been described. Nevertheless, it will be understood that various modifications may be made without departing from the spirit and scope of the invention. Accordingly, other embodiments are within the scope of the following claims.

What is claimed is:

1. A method of making a compound comprising reacting a compound of formula (II),

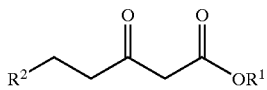

(II)

wherein

R$^1$ is independently alkyl, alkenyl, alkynyl, cycloalkyl, arylalkyl, or heteroarylalkyl;

R$^2$ is independently alkyl, aryl, arylalkyl, heteroaryl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)$_n$R$^6$, NO$_2$, CN, halo, NR$^6$C(O)R$^6$, or NR$^6$S(O)$_n$R$^6$;

Each R$^6$ is independently alkyl, alkenyl, alkynyl, cycloalkyl, aryl, heterocyclyl, arylalkyl, or heteroarylalkyl, each optionally substituted with 1–4 independent substituents selected from the group hydroxy, mercapto, amino, alkoxy, carboxylic acid, ester, amido, N-alkyl-substituted amido, halo, nitro, and nitrile; and n is 1 or 2;

with a chiral borane reducing agent to give a compound of formula (I):

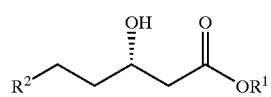

(I)

wherein R$^1$ and R$^2$ are as defined above.

2. The method of claim 1, wherein the reacting is performed at room temperature.

3. The method of claim 1, further comprising converting a compound of formula (I) to a compound of formula (III):

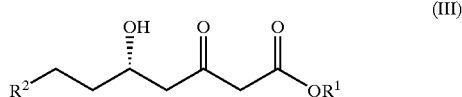

(III)

wherein

R$^1$ is independently alkyl, arylalkyl, or heteroarylalkyl;

R$^2$ is independently alkyl, aryl, arylalkyl, heteroaryl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)$_n$R$^6$, NO$_2$, CN, halo, NR$^6$C(O)R$^6$, or NR$^6$S(O)$_n$R$^6$;

Each R$^6$ is independently alkyl, alkenyl, alkynyl, cycloalkyl, aryl, heterocyclyl, arylalkyl, or heteroarylalkyl, each optionally substituted with 1–4 independent substituents selected from the group hydroxy, mercapto, amino, alkoxy, carboxylic acid, ester, amido, N-alkyl-substituted amido, halo, nitro, and nitrile; and n is 1 or 2.

4. The method of claim 3, wherein the compound of formula (I) is reacted with a nucleophile, or salt thereof, of formula (IV):

(IV)

wherein

R$^1$ is independently alkyl, arylalkyl, or heteroarylalkyl; to give the compound of formula (III).

5. The method of claim 4, wherein the nucleophile is the lithium salt of the t-butylacetate anion.

6. The method of claim 1, further comprising converting a compound of formula (I) to a compound of formula (V):

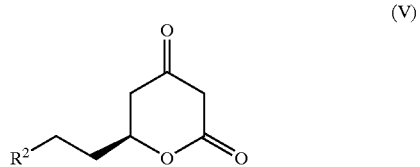

(V)

wherein

R$^2$ is independently alkyl, aryl, arylalkyl, heteroaryl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)NR$^6$, NO$_2$, CN, halo, NR$^6$C(O)R$^6$, or NR$^6$S(O)$_n$R$^6$;

Each R$^6$ is independently alkyl, alkenyl, alkynyl, cycloalkyl, aryl, heterocyclyl, arylalkyl, or heteroarylalkyl, each optionally substituted with 1–4 independent substituents selected from the group hydroxy, mercapto, amino, alkoxy, carboxylic acid, ester, amido, N-alkyl-substituted amido, halo, nitro, and nitrile; and n is 1 or 2.

7. The method of claim 6, wherein the converting comprises reacting with an acid catalyst.

8. The method of claim 7, wherein the acid catalyst is an organic acid.

9. The method of claim 7, wherein the acid is an acetic acid or a sulfonic acid.

10. The method of claim 7, wherein the acid catalyst is trifluoroacetic acid, p-toluenesulfonic acid, or camphorsulfonic acid.

11. The method of claim 1, further comprising converting a compound of formula (I) to a compound of formula (VI):

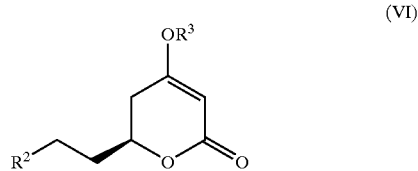

wherein
R² is independently alkyl, aryl, arylalkyl, heteroaryl, heteroarylalkyl, each optionally substituted with 1 to 4 independent NR⁶R⁶, C(O)NR⁶R⁶, OR⁶, SR⁶, C(O)OR⁶, C(O)R⁶, S(O)$_n$R⁶, NO₂, CN, halo, NR⁶C(O)R⁶, or NR⁶S(O)$_n$R⁶;
n is 1 or 2;
R³ is independently H, alkyl, arylalkyl, heteroarylalkyl, each optionally substituted with 1 to 4 independent NR⁶R⁶, C(O)NR⁶R⁶, OR⁶, SR⁶, C(O)OR⁶, C(O)R⁶, S(O)$_n$R⁶, NO₂, CN, halo, NR⁶C(O)R⁶, or NR⁶S(O)$_n$R⁶; and
Each R⁶ is independently alkyl, alkenyl, alkynyl, cycloalkyl, aryl, heterocyclyl, arylalkyl, or heteroarylalkyl, each optionally substituted with 1–4 independent substituents selected from the group hydroxy, mercapto, amino, alkoxy, carboxylic acid, ester, amido, N-alkyl-substituted amido, halo, nitro, and nitrile.

12. The method of claim 11, wherein the converting comprises reacting with an alkylating agent in the presence of a base.

13. The method of claim 12, wherein the alkylating agent is an alkyl halide.

14. The method of claim 12, wherein the alkylating agent is an alkyl sulfate.

15. The method of claim 1, wherein the chiral borane reducing agent is a borane-dimethylsulfide complex.

16. The method of claim 1, wherein the chiral borane reducing agent is a borane-dimethylsulfide complex derived from a chiral 2-pyrrolidinemethanol derivative.

17. The method of claim 1, wherein the chiral borane reducing agent is an oxazapyrrolidinyl borane.

18. The method of claim 1, wherein the chiral borane reducing agent is a borane-dimethylsulfide complex derived from (S)-(−)-α,α,-diphenyl-2-pyrrolidinemethanol.

19. The method of claim 1, wherein the chiral borane is derived from (S)-(−)-α,α,-diaryl-2-pyrrolidinemethanol.

20. The method of claim 1, wherein the chiral borane is derived from (S)-(−)-α,α,-dialkyl-2-pyrrolidinemethanol.

21. The method of claim 1, wherein the compound is a kavalactone.

22. The method of claim 1, wherein the compound is a compound present in the extract of kava kava.

23. A method of making a kavalactone comprising the method of claim 1.

24. A method of making a kavalactone comprising the method of claim 3.

25. A method of making a kavalactone comprising the method of claim 6.

26. A method of making a kavalactone comprising the method of claim 11.

27. A method of making an enantio-enriched kavalactone comprising the method of claim 1.

28. The method of claim 1, wherein the kavalactone is dihydrokawain.

29. The method of claim 1, wherein the kavalactone is (S)-(+)-dihydrokawain.

30. The method of claim 1, wherein the kavalactone is dihydrokawain or dihydromethysticin.

31. The method of claim 1, wherein the compound is a kavalactone derivative compound.

32. The method of claim 1, wherein the compound is a dihydrokawain derivative compound.

33. The method of claim 1, wherein the compound is an active kavalactone derivative compound.

34. A method of making a compound comprising reacting a compound of formula (VIII):

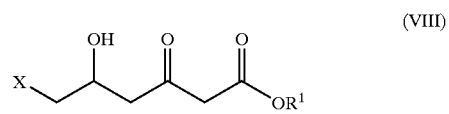

wherein
R¹ is independently alkyl, arylalkyl, or heteroarylalkyl;
X is a leaving group;
with a chiral borane reducing agent to give a compound of formula (VII)

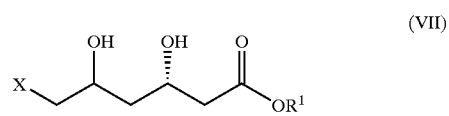

wherein R¹ and X are as defined above.

35. The method of claim 34, wherein the reacting is performed at room temperature.

36. The method of claim 34, further comprising converting a compound of formula (VII) to a compound of formula (IX):

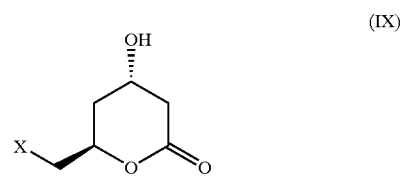

wherein X is a leaving group.

37. The method of claim 34, further comprising converting a compound of formula (VII) to a compound of formula (X):

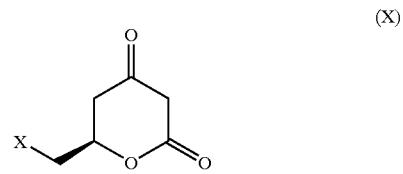

wherein
X is a leaving group.

38. The method of claim 37, wherein the converting comprises reacting with an oxidizing agent.

39. The method of claim 34, further comprising converting the compound of formula (VII) to a compound of formula (XI):

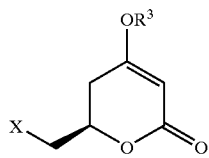
(XI)

wherein

R$^3$ is independently H, alkyl, arylalkyl, heteroarylalkyl; and

X is a leaving group.

40. The method of claim 39, wherein the converting comprises reacting with an alkylating agent in the presence of a base.

41. The method of claim 34, further comprising converting the compound of formula (VII) to a compound of formula (XII):

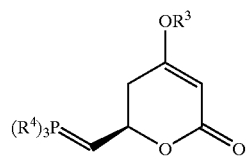
(XII)

wherein

R$^3$ is independently H, alkyl, arylalkyl, heteroarylalkyl; and each R$^4$ is independently alkyl or aryl.

42. The method of claim 41, wherein the converting comprises reacting with a triaryl-substituted phosphine.

43. A method of making a compound comprising reacting a compound of formula (XIV):

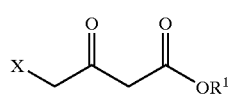
(XIV)

wherein

R$^1$ is independently alkyl, arylalkyl, or heteroarylalkyl; and

X is a leaving group;

with a chiral borane reducing agent to give a compound of formula (XIII):

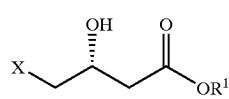
(XIII)

wherein R$^1$ and X are as defined above.

44. The method of claim 43, further comprising converting a compound of formula (XIII) to a compound of formula (XV):

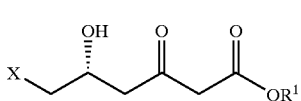
(XV)

wherein

R$^1$ is independently alkyl, arylalkyl, or heteroarylalkyl; and

X is a leaving group.

45. The method of claim 44, wherein the compound of formula (XIII) is reacted with a nucleophile, or salt thereof, of formula (IV):

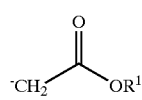
(IV)

wherein

R$^1$ is independently alkyl, arylalkyl, or heteroarylalkyl; to give the compound of formula (XV).

46. The method of claim 43, further comprising converting a compound of formula (XIII) to a compound of formula (XVI):

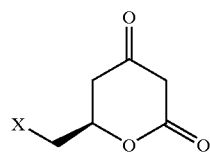
(XVI)

wherein

X is OR$^6$; and

Each R$^6$ is independently alkyl, alkenyl, aryl, arylalkyl, or heteroarylalkyl, each optionally substituted with 1–4 independent substituents selected from the group hydroxy, mercapto, amino, alkoxy, carboxylic acid, ester, amido, N-alkyl-substituted amido, halo, nitro, and nitrile.

47. The method of claim 46, wherein the converting comprises reacting with an acid catalyst.

48. The method of claim 34, further comprising converting a compound of formula (XIII) to a compound of formula (XVII):

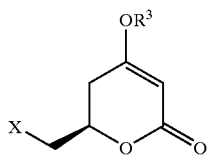
(XVII)

wherein

X is OR$^6$;

R$^3$ is independently H, alkyl, arylalkyl, heteroarylalkyl, each optionally substituted with 1 to 4 independent NR$^6$R$^6$, C(O)NR$^6$R$^6$, OR$^6$, SR$^6$, C(O)OR$^6$, C(O)R$^6$, S(O)$_n$R$^6$, NO$_2$, CN, halo, NR$^6$C(O)R$^6$, or NR$^6$S(O)$_n$R$^6$;

n is 1 or 2; and

Each R$^6$ is independently alkyl, alkenyl, aryl, arylalkyl, or heteroarylalkyl, each optionally substituted with 1–4 independent substituents selected from the group hydroxy, mercapto, amino, alkoxy, carboxylic acid, ester, amido, N-alkyl-substituted amido, halo, nitro, and nitrile.

49. The method of claim 48, wherein the converting comprises reacting with an alkylating agent in the presence of a base.

50. The method of claim 43, further comprising converting a compound of formula (XIII) to a compound of formula (XVIII):

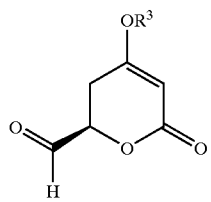

(XVIII)

wherein $R^3$ is independently H, alkyl, arylalkyl, heteroarylalkyl, each optionally substituted with 1 to 4 independent $NR^6R^6$, $C(O)NR^6R^6$, $OR^6$, $OR^6$, $SR^6$, $C(O)OR^6$, $C(O)R^6$, $S(O)_nR^6$, $NO_2$, CN, halo, $NR^6C(O)R^6$, or $NR^6S(O)_n R^6$;

n is 1 or 2; and

Each $R^6$ is independently alkyl, alkenyl, aryl, arylalkyl, or heteroarylalkyl, each optionally substituted with 1–4 independent substituents selected from the group hydroxy, mercapto, amino, alkoxy, carboxylic acid, ester, amido, N-alkyl-substituted amido, halo, nitro, and nitrile.

51. The method of claim 50, wherein the converting comprises reacting with an oxidizing agent.

* * * * *